United States Patent [19]

Renn et al.

[11] 3,966,897

[45] June 29, 1976

[54] MEDIUM FOR USE IN BIOASSAY AND METHOD OF USING SAME

[75] Inventors: Donald W. Renn, Glen Cove, Me.; Calvin A. Saravis, Waban, Mass.

[73] Assignee: Marine Colloids, Inc., Rockland, Maine

[22] Filed: Apr. 2, 1973

[21] Appl. No.: 346,966

[52] U.S. Cl. .............................. 424/1.5; 23/230 B; 252/408; 424/1; 424/8; 424/12

[51] Int. Cl.² .................. G01N 33/00; A61K 43/00; G21H 5/02

[58] Field of Search ............ 252/316, 408, 301, 1 S; 424/12, 1; 23/230 B

[56] References Cited
UNITED STATES PATENTS

| | | | |
|---|---|---|---|
| 2,358,549 | 9/1944 | Wenck | 252/316 X |
| 2,385,363 | 9/1945 | Laliberte | 252/316 X |
| 2,487,077 | 11/1949 | Shepherd | 252/408 X |
| 3,043,751 | 7/1962 | Goldman | 252/408 X |
| 3,063,916 | 11/1962 | Kosikowski | 252/408 X |
| 3,179,600 | 4/1965 | Brockett | 252/316 X |
| 3,453,180 | 7/1969 | Fraser | 252/408 X |
| 3,527,712 | 9/1970 | Renn et al. | 252/316 |
| 3,531,254 | 9/1970 | Okuda | 252/408 X |
| 3,553,310 | 1/1971 | Csizmas et al. | 424/12 X |
| 3,578,604 | 5/1971 | Uriel et al. | 252/316 |
| 3,639,558 | 2/1972 | Csizmas et al. | 424/12 |
| 3,641,235 | 2/1972 | Weiss | 424/11 X |
| 3,646,346 | 2/1972 | Catz | 424/1 X |
| 3,654,090 | 4/1972 | Schuurs et al. | 424/12 X |
| 3,714,344 | 1/1973 | Brown | 424/1 |
| 3,793,445 | 2/1974 | Updike et al. | 424/12 |

FOREIGN PATENTS OR APPLICATIONS

| | | | |
|---|---|---|---|
| 158,476 | 8/1954 | Australia | 252/408 |
| 953,414 | 3/1964 | United Kingdom | 210/321 |
| 1,248,764 | 10/1971 | United Kingdom | 424/1 |
| 1,248,765 | 10/1971 | United Kingdom | 424/1 |

OTHER PUBLICATIONS

Crowle, *Immunodiffusion*, 1961, Academic Press, pp. 202–223.

Wide, "Radioimmunoassays Employing Immunosorkents," Acta. Endocrinologua Supplementum, No. 142, 1969, pp. 207–221.

Wide, "Solid Phase Antigen–Antibody Systems" from *Radioimmunoassay Methods*, 1970, pp. 405–412.

Crowle, "Four Modifications of the Micro Agar Diffusion Pricipition Test, In Journal of Lab. & Clin. Med. vol. 55, No. 4, Apr. 1960, pp. 594–604.

Lehnenger, Albert L., Biochemistry, N.Y., Worth Pulilishers, Inc., p. 132.

*Primary Examiner*—Benjamin R. Padgett
*Assistant Examiner*—Christine M. Nucker

[57] ABSTRACT

A hydratable or hydrated gel medium for use in bioassay of a test substance contains fixed in a localized zone a reagent for the test substance. Assays are conducted rapidly by diffusing the test substance followed by an indicator substance also reactive with the reagent into the zone and measuring a change in characteristics within the zone caused by the reaction of the indicator substance.

11 Claims, No Drawings

MEDIUM FOR USE IN BIOASSAY AND METHOD OF USING SAME

This invention relates to media for use in direct and indirect bioassay processes and to the method of making and using such media.

Competitive radioimmunoassay has been employed as an analytical technique for several years and the general procedure has been extended into non-immune systems as described by Solomon A. Berson and Rosalyn S. Yalow in IMMUNOBIOLOGY, R. A. Good and D. W. Fisher, Editors, Chapter 30, "Radio-immunoassay-Current Status", pages 287–293, (Sinauer Associates, Inc., Stamford, Conn.). As conventionally carried out, competitive radioassay procedures involve mixing a sample of solution containing a test substance, e.g., a hormone, with specific known amounts of antibody followed by the corresponding radioactively labelled hormone to which the antibody was made, after which the mixture is incubated for an extended period of time, usually a day or more, to permit the labelled hormone to compete with the unlabelled hormone in approximate proportion to their relative concentrations for binding the antibody. Thereafter the residual labelled free hormone is separated from the mixture, e.g., by adsorption on talc or charcoal, by paper chromatoelectrophoresis or double antibody precipitation, and the radioactivity in the complex of bound hormone-antibody is measured with an isotope counter. By comparing the count with that obtained using a solution containing a known quantity of hormone, the amount of hormone in the test sample is determined. Another method for performing the competitive radioimmunoassay includes mixing of specific amounts of labelled antigen with the test sample containing unknown amounts of unlabelled antigen, then bringing both simultaneously into reaction with the antibody and finally following the previously described separation and counting procedure. In still another competitive assay procedure, the test antigen can be brought into contact with a complex consisting of the labelled antigen and specific antibody. The amount of radioactivity released is proportional to the concentration of the antigen in the test solution.

Non-competitive or so-called sandwich technique radioimmunoassays are also used to determine the concentration of an antigen in test samples. In this technique the antigen in the sample is first reacted with immobilized antibody to form an antigen-antibody complex. Radioactive antibody, either antigen specific or antibody specific, is caused to react with the complex, whereupon the labelled antibody occupies a number of sites proportional to the amount of antigen in the test solution and can be measured after removing the unreacted labelled antibody by washing.

The competitive and non-competitive assays may involve the use of indicators other than radioactivity. U.S. Pat. No. 3,641,235 describes the use in filter paper of indicator dyes attached to immobilized antigens (or antibodies) which release in proportion to the amount of antibody (or antigen if the antibody is immobilized). The released dye can then be measured by fluorimetry, spectrophotometry, refractometry or the like and related to concentration of the antigen (or antibody) being determined. U.S. Pat. No. 3,654,090 describes the determination of a component of the antigen-antibody reaction using one component (antigen or antibody) in an insolubilized form and the other one covalently linked to an enzyme. The enzyme such as glucose oxidase, peroxidase, etc. is released upon reaction and can be determined by a reaction either with a colored substrate, or it may itself yield a colored end product, as described for example in Weiss U.S. Pat. No. 3,641,235 in which there is described the application to a strip of filter paper a mixture of immunological reagent particles and fluorescein, after which the fluorescein is released and transported by capillary movement of an antiserum sample. A variety of such reactions are known. In addition, direct measurements of the captured or released materials, or of materials which after release have been recaptured, can be made where applicable by refractometry, interferometry, fluoresence, bioassay or spectrophotometry, turbidimetry, bioluminescence, etc.

The assays described are not limited to immune systems. Enzymes and their substrates can be determined as well. In these determinations the enzyme or substrate is insolubilized depending upon which substance is to be determined. If the enzyme is to be determined, the substrate is insolubilized. If the substrate is to be determined, the enzyme is insolubilized. The test solution is brought into contact with the immobilized enzyme (or substrate) whereupon reaction occurs forming an immobilized complex. Radioactively labelled substrate (or enzyme) is introduced and reacts at unoccupied sites. Determination of the radioactivity in the complex gives a measure of the amount of enzyme (or substrate) in the test sample. In a modification of this procedure, a specific amount of the radioactively labelled enzyme (or substrate) can be added directly to the test sample and a competitive one step reaction effected after which determination of the radioactivity present in the immobilized complex provides a measure of the enzyme in the test solution. Indirectly, enzyme inhibitors can be measured by these processes by determining the degree to which the enzyme-substrate complexing is inhibited and comparing with proper controls.

All of these bioassay procedures involve in common the reaction of the test substance with an appropriate reagent, e.g., hormone-antibody, antigen-antibody, enzyme-substrate, or their converse reactions, together with direct or indirect quantitative measurement of the amount of reagent so reacted by measurement of a characteristic of the reagent (or of another substance, an indicator, which has reacted with the reagent), such as color, radioactivity, or other physical characteristics.

The present invention provides a solid medium, preferably a gel medium, for use in such assay procedures in which there is disposed in contact with the medium and fixed against diffusive movement therethrough a fixed quantity of desired reagent capable of reaction with the test substance, the reagent being confined to a localized, restricted or defined zone or aea of the medium. The reagent is immobilized or fixed against diffusive movement through or across the medium preferably either by bonding it chemically to the substance of the medium or by bonding it chemically or physically, e.g. by adsorption to a particulate solid material insoluble in the gel medium, the particles being dispersed or embedded in the zone or area of medium and being sufficiently large, i.e., having at least one dimension greater then 0.01 so that they are incapable of substantial movement through the medium at ordinary temperatures, i.e., from 0° to 60°C., the particles thus serving as anchors to fix the reagent in place in the desired zone or area of the medium.

The medium can be used in bioassay procedures by applying to it a sample of the test substance and a known quantity of an indicator substance also capable of reacting with the reagent. In the preferred method, the indicator is applied to the medium at a zone or area more remote from that of the reagent than is the test substance so that the test substance will come into contact with and react with the reagent before the indicator reaches and reacts with it. Diffusion of the test substance and of the indicator through or across the medium so as to react sequentially with the fixed reagent can be accelerated by any of the usual means such as gravity, centrifugal force, osmotic pressure, or electrical field. After the test substance in the sample has completely reacted with the fixed reagent and the indicator substance has reacted sequentially with the excess or remainder of the fixed reagent, the residual unreacted indicator is removed from the zone or area by washing and/or continuance of the diffusion process. The amount of the indicator which has reacted with the reagent and which consequently remains in the desired zone or area is then measured by determining a suitable characteristic such as radioactivity. From this value it is possible to determine the proportion of the fixed reagent which first reacted with the test substance, hence the quantity of the test substance present in the sample.

The medium of the present makes possible a great increase in the speed of the assay procedure, shortening the total time required to as little as 2 hours or even less, and in addition eliminates the precipitation step and separation of the precipitate which is involved in many of the conventional assay procedures. The medium may be any of the solid media commonly employed for molecular diffusion procedures such as any of the usual materials which form gels when exposed to water or aqueous systems and which are commonly employed as media for chromatography or electrophoresis. Such materials include cellulosic materials such as micro-crystalline regenerated cellulose, hydroxypropyl cellulose, carboxymethyl cellulose, and diethylaminoethyl cellulose, as well as non-cellulosic materials such as polymers and copolymers of acrylamide, hydroxyacrylate or hydroxymethacrylate polymers or copolymers, gelatin, and various polysaccharides such as starch, dextran, agar, agarose and carrageenan, cross-linked forms of any of the foregoing as well as other water sorptive gel-forming solid materials as well as mixtures of any two or more of the foregoing. The medium preferably is in the form of a sheet, film or layer of the material of the order of 0.1 to 2 millimeters in thickness when hydrated and supported on a relatively stiff backing sheet or film such as glass or polyester or cellulose acetate film of the type used for photographic film, which support is inert to the test substances and reagents employed.

The reagent which is fixed or anchored in the gel medium may be any of those employed in conventional assay procedures. In general, these reagents are proteinaceous or peptidal, steroidal, terpenoidal, polynucleosidic carbohydrate, or polysaccharide materials, the precise identity in each case depending, as is well known, on the identity of the test substance. For example, in an immune system, for test substances containing antigens such as hormones, the reagent employed is the appropriate antibody; among the hormones to which the procedure has been applied are insulin, ACTH, parathyroid hormone, glucagon, proinsulin, vasopressin, oxytocin, gastrin, calcitonin, testosterone, estradiol, aldosterone, estrone, and dihydrotestosterone. Antibodies are also used as reagents in immune systems for other antigens such as intrinsic factor, esterases and other enzymes, digitoxin, Australian antigen, alkaline phosphatase, tumor-associated antigens such as alpha fetoglobulin, carcinoembryonic antigen, and other tumor-associated antigens, rheumatoid factor, folic acid, neurophysin and morphine. In non-immune systems in which the test substance is a hormone such as thyroxine, cortisol, corticosterone, cortisone, 11-desoxycortisol, or progesterone, there may be used as the reagents any of the specific binding proteins in plasma, as is well known, while for test substances such as vitamin $B_{12}$, folic acid, cyclic AMP, GMP, or messenger RNA, there may be used as the reagent, respectively, intrinsic factor, FA reductase, phosphodiesterases, and complementary DNA. Similarly, for test substances which are enzymes, the corresponding substrate may be used as the reagent. It is also possible in all cases to reverse the procedure, e.g., when the test substance contains an antibody or binding protein from plasma, the corresponding antigen or hormone can be used as the reagent.

The reagent may be chemically bonded to the material of the medium itself, using appropriate coupling agents which do not interfere with its reactivity toward the test substance, or it may be chemically bonded, either directly or by means of appropriate coupling agents, to a solid material different from and insoluble in the material of the medium, which solid material is embedded or dispersed in the medium and is in the form of sufficiently large particles or pieces (at least the dimension greater than 0.01 micron) so as to be immobile and incapable of movement by diffusion through the medium even under the influence of the accelerating forces employed during the test procedure. It may also be adsorbed onto the surfaces of or absorbed into certain solid materials and held there by physical or chemico-physical forces which are not primary valence bonds. In addition, in the case of some reagents, it is possible by reacting them with appropriate chemical cross-linking agents to convert them into insoluble solid materials which, while retaining their desired reactivity with the test substance, are in the form of sufficiently large molecules or particles to be immobilized within or on the surface of the medium and not subject to transport by diffusion.

The size and shape of the zone or area of the medium within which the reagent is confined or fixed is a matter of choice provided that it is less than all of the medium. It may and preferably does extend throughout the thickness of the medium when the latter is in the form of a sheet or film, and its location, size and shape as well as the number and spacing when more than one is present can be varied depending upon whether or not external forces are to be applied to accelerate diffusion during the assay procedure, and to facilitate proper positioning of the sample of test substance and of other substances for rapid and effective conduct of the assay.

The coupling agents which can be used to bond the reagent chemically to the material of the medium or to another solid material are well known and function through well known reactive groups. In the case of materials containing hydroxyl groups such as cellulosic materials and polysaccharides, cyanogen halides such as cyanogen bromide can be used as the binding agent by reacting it first with the hydroxyl-containing material, then bringing proteinaceous or peptidal reagent into contact with the thus activated material. In the case of acrylamide polymers, glutaraldehyde may be similarly used as a binding agent by first reacting it with the polymer. It is also possible to react the hydroxyl-containing materials, after activation with cyanogen bromide, with alkylene diamines, then couple them to proteinaceous reagents by using a water-soluble carbodiimide, or an 0-bromoacetyl-N-hydroxysuccinimide as coupling agent. The latter coupling agent can also be used to couple with reagents which contain peptide, amino, phenolic hydroxyl, or imidazole groups. Other coupling agents which can be used to replace the foregoing for coupling to a variety of reagents include succinic anhydride, diazotizing agents, and mercapto compounds, as taught by Cuatrecasas, Nature, 228, 1327–8, and Biochemistry, 11 (12), 2291–9. Many other coupling agents and processes have been described in the literature for chemically bonding materials containing hydroxyl groups to enzymes, antibodies, antigens, steroidal hormones, proteins, and peptides.

The solid materials onto the surfaces of which the reagents can be adsorbed for embedding in the gel material can be in the form of films, sponges, sieves, gauzes, fibrous webs or the like but are preferably in the form of small particles ranging in size from 0.01 microns to 100 mils or more in diameter in order to provide a large surface to volume ratio. Among useful materials are Fuller's earth, talc, porous glass beads, hydroxy apatite, zirconyl phosphate, charcoal, polyethylene, polypropylene, or polystyrene particles, ion-exchange resins such as polysulfonate or polycarboxylate resins, diethylaminoethyl cellulose, or the like.

Reagents which can be insolubilized by reaction with cross-linking agents comprise antibodies, enzymes, and proteins, including protein antigens, all of which can be reacted with such cross-linking agents as glutaraldehyde or ethyl chloroformate, or glyoxal.

The bound reagents may be placed in or confined to a localized zone of the medium by various means. For example, the binding agent may be reacted with a solid material in the form of a sheet, web, sponge, sieve, gauze or in the form of a mass of granules or particles after which the solution of reagent is brought into contact therewith (e.g., by electrophoresis or diffusion) and allowed to react so as to become bonded thereto. A measured quantity of this complex can then be fixed in or adhered to any desired portion or zone of a conventional sheet or layer of gel medium used for chromatography or electrophoresis. A plug or insert of the complex of the appropriate size and shape can be inserted in a well or opening cut in a conventional sheet or layer of medium and can be bonded or adhered in place, or the well can be filled with a mass of the complex in granular form which is adhered in place by any suitable adhesive, including gel-forming materials of the same type useful for forming the medium itself. The gel-forming material is normally tacky when swollen with water and is readily adherent to itself under these conditions. A layer of granules or particles of the complex may also be bonded to the surface of a conventional sheet or layer of gel-forming material, being confined to the desired location by means of a fence or jig or other masking device until it has become adequately adhered.

Instead of bonding a plug of complex into a well in a conventional sheet of medium, the plug may be adhered by conventional procedures to a suitable backing or support sheet, e.g., glass or polyester such as polyethylene terephthate, and then a sheet or layer of conventional gel-forming material can be formed or deposited on the backing around the plug. It is also possible to bring the binding agent into contact with only a restricted localized zone of a conventional sheet or film of paper or cellulosic material or of hydrated or hydratable gel material, the extent of contact (and hence of reaction) being confined to the desired zone by means of a mask or jig, and thereafter to bring the desired reagent (or a solution thereof) into contact with the same zone to cause the reagent to become bonded in that zone only.

In the case of media made of gel-forming materials which can be dried for storage and then rehydrated immediately prior to use, as for example agarose made in accordance with U.S. Pat. No. 3,527,712, the medium of the present invention containing reagent bonded to a localized zone thereof can also be dried, for example by lyophilization, for storage and can be rehydrated shortly before use for radioassay molecular diffusion procedures. In a preferred embodiment, the medium of the present invention consists essentially of an inert flexible backing or support film to one face of which is bonded a layer or sheet of dried rehydratable agarose having a localized zone of restricted area much smaller than the total area of the layer or sheet within which zone there is bound to the agarose, either at the exposed surface of the layer or throughout the body of the layer or both, the desired reagent.

The medium of the present invention is used for bioassay by first hydrating it, in the case of media in the form of dry hydratable gel-forming materials, and then applying a sample of the test substance, which may be but need not be in the form of a solution or dispersion in water or in an aqueous medium, the sample being applied either directly to the zone containing the fixed reagent or to a portion of the medium spaced from the margin of the zone, after which it is permitted or caused to diffuse into the zone by conventional procedures to enter into the desired reaction. The amount or proportion of the fixed reagent which has reacted is then measured by any of the direct or indirect procedures described, using appropriate indicators as desired. When an indicator material is used, it is brought into contact with the zone containing the fixed reagent, after the test substance has reacted with the reagent, in order to react irreversibly with residual reagent, and any excess of the indicator is removed by diffusion out of the zone into the other portion of the medium, or indeed out of the medium completely, using any of the conventional means for accelerating diffusion if desired. The amount of indicator remaining in the zone is then determined by measurement of its characteristic property--e.g., radioactivity, biological or chemical activity, color, luminescence, fluorescence, or light refractivity. The results can be compared with those obtained by following the same procedures but using control samples containing known quantities of the test substance.

The following specific examples are intended to illustrate more fully the nature of the invention without acting as a limitation upon its scope.

EXAMPLE 1

Beads of aqueous agarose gel such as those used for affinity chromatography are activated by reacting with cyanogen bromide, then reacted or coupled with antibody associated with hepatitis (HB Ab) to bond the antibody reagent to the agarose. The beads are then suspended in an aqueous solution (0.5%) of agarose at 37°C. which is then poured into a petri dish and allowed to gel, forming a layer about 1 mm. thick containing the antibody reagent fixed within it.

A conventional counterelectrophoresis strip (MCI Biomedical Type 35-II) consisting of a layer of dried rehydratable agarose prepared as described in U.S. Pat. No. 3,527,712 bonded to a flexible polycarbonate support film having a row of spaced wells 4 mm. in diameter arranged along each margin, opposite each other, is immersed in water for 45 minutes to rehydrate it, then in 0.05 molar sodium barbital at pH 8.2 for 15 minutes to prepare it for electrophoresis.

Discs 4 mm. in diameter are cut from the layer of gel containing the fixed antibody reagent by means of a cork borer, and each disc is placed in a well on the anodal side of the strip and adhered in place with a warm aqueous solution of agarose to provide a capture zone.

The medium thus prepared is used for measuring hepatitis antigen in test substances, i.e., the sera of patients, by placing 10 microliters of each sample of serum in a cathodal well of the medium opposite one of the plugs containing fixed antibody. A standard sample containing a known quantity of hepatitis associated antigen (HB Ag) is placed in another of the cathodal wells, and in still another is placed a negative control. The strip thus prepared is placed in a standard electrophoresis apparatus using a buffer solution the same as that with which the strip was equilibrated and subjected to electrophoresis for 60 minutes at 45 ma and 30 V. D.C. At this point there is introduced into each of the cathodal wells 10 microliters of a standard indicator solution of radio-labelled antigen (HB Ag containing bound $I^{125}$) and electrophoresis is continued for another 60 minutes.

The medium or strip is then removed from the electrophoresis unit, washed for 2 hours with stirring in aqueous 0.85% sodium chloride, rinsed in distilled water, and dried in air at 60°C. Each of the capture zones containing the fixed antibody is then removed by means of a punch and counted in an isotope counter. The results obtained from the test substances can be compared with the results from the known control and the negative control.

If desired, a series of known samples of different amounts of HB Ag can be subjected to the procedure to provide a standardization or calibration curve to facilitate precise movement of unknown samples.

EXAMPLE 2

Beads of aqueous agarose gel are activated with cyanogen bromide as in Example 1, then reacted or coupled with purified gamma globulin (Ig G) reagent. The beads are then fixed in a well of a conventional electrophoresis strip as described in the preceding Example to provide a medium having a plurality of capture zones, each containing fixed Ig G reagent, along the cathodal side of the strip.

The medium thus prepared is used for detection and analysis of antibodies to gamma globulin by placing 10 microliters of each of the test samples of patient serum in the opposing wells on the anodal side of the strip and subjecting the strip to electrophoresis as in the preceding example, followed by adding 10 microliters of solution of radioactive anti-IgG antibodies as an indicator, further electrophoresis, washing, drying and counting as before. A sample or series of samples of solutions containing known quantities of antibodies are used for calibration.

EXAMPLE 3

A medium having capture zones is prepared as described in the preceding two examples except that anti alpha-1-fetoglobulin antiserum is used as the reagent. The medium or strip thus prepared can be used for determination of the tumor-associated antigen known as alpha-1-fetoglobulin, employing radioactive alpha-1-fetoglobulin as the indicator. The results are compared with a calibration curve prepared using samples containing various known quantities of the antigen.

EXAMPLE 4

A medium having capture zones is prepared as described in Example 1 except that the agarose beads, after activation by reacting with cyanogen bromide, are further reacted with $NH_2(CH_2)_{10}NH_2$, then coupled with the HB Ab using 1-ethyl-3-(3'dimethylaminopropyl)-carbodiimide. The medium can be used in the same manner as described in Example 1.

EXAMPLE 5

A medium is prepared as described in Example 1 except that there is used instead of the beads of aqueous agarose gel beads of cross-linked dextran aqueous gel. The medium is used as described in Example 1.

Similarly, there can be substituted for the beads of agarose in Example 4 porous glass beads or cross-linked dextran beads activated with p-isothiocyanatophenoxy hydroxy propyl chloride. Also, the antibody and antigen of Example 1 can be interchanged, i.e., the antigen can be fixed in the medium and used as the reagent for a test substance containing the antibody. The beads of agarose of Example 1 can also be replaced by particles of cellulose and the cyanogen bromide replaced by chloro-s-triazine, cyanuric chloride, or 1-(m-nitrobenzyloxy) methyl pyridinium chloride. The agarose beads can be replaced by particles of nylon (a superpolyamide) or by particles of aqueous polyacrylamide gel or of diethylaminoethyl cellulose and the cyanogen bromide replaced by glutaraldehyde. The cyanogen bromide of Example 1 can also be omitted and there can be used, in place of the agarose beads, beads of E-aminocaproyl-D-tryptophan methyl ester of agarose, or beads of N-hydroxysuccinimiide ester of succinylated aminoalkyl agarose, or of polypropylene or polystyrene, the latter two polymers adsorbing the antibody on their surfaces. The cyanogen bromide and agarose beads of Example 1 can be replaced by zirconyl phosphate or by tanned red blood cells.

In Example 4, the carbodiimide can be replaced by 0-bromoacetyl-N-hydroxysuccinimide.

There may also be used in place of the antibody reagent of Example 1 an antibody containing an indicator dye as described in U.S. Pat. No. 3,641,235; in this case the radioactive indicator need not be used, the color liberated by the antigen of the test substance being used as the indicator. Similarly, a conjugate of antibody and enzyme as described in U.S. Pat. No.

3,654,090 can be used as the reagent in place of the antibody of Example 1; the radioactive indicator can be dispensed within this case also, the enzyme released from the conjugate by the test substance containing the antigen serving as the indicator.

Glucose oxidase can be substituted for the antibody in Example 1 and used as a fixed reagent to detect and measure glucose in a test sample, a leuco dye solution being used as the indicator for the hydrogen peroxide released from the reagent by the glucose. To determine the enzyme pyruvic kinase (PK) in a test substances, phosphoenolpyruvate substrate can be substituted for the antibody in Example 1, and a solution of adenosine diphosphate used along with the test substance. The pyruvate released can be determined using as an indicator an enzyme such as lactic dehydrogenase and standard color reagents.

What is claimed is:

1. A medium for use in bioassay diffusion processes with test substances, said medium comprising a layer of dry material hydratable to a gel through which said test substance can diiffuse, and fixed to a restricted localized zone of said layer against diffusive movement therethrough a reagent capable of reaction with said test substance, said reagent being confined to said zone which is smaller than said layer.

2. A medium for use in bioassay diffusion processes with test substances, said medium comprising a layer of hydrated gel material through which said test substance can diffuse, and fixed to a restricted localized zone of said layer against diffusive movement therethrough a reagent capable of reaction with said test substance, said reagent being confined to said zone which is smaller than said layer.

3. A medium as claimed in claim 1 in which said reagent is an antibody, an antigen, an enzyme, or an enzyme substrate.

4. A medium as claimed in claim 1 in which said reagent is proteinaceous.

5. A medium as claimed in claim 1 in which said hydratable material is an organic polymer.

6. A medium as claimed in claim 1 in which said hydratable material is an organic hydroxy-containing polymer, and said reagent is proteinaceous and is bound to said polymer by means of a cyanogen halide bonding agent.

7. A medium as claimed in claim 1 in which said hydratable material is a polymer of acrylamide, and said reagent is proteinaceous and is bound to said polymer by means of glutaraldehyde bonding agent.

8. A medium as claimed in claim 1 in which said layer is a cellulosic material, a polysaccharide or a polymer of acrylamide.

9. The method of conducting a bioassay of a test substance which comprises providing a medium as claimed in claim 2, applying to said medium a sample of said test substance and an indicator substance also capable of reacting with said reagent, at least said indicator substance being applied to said medium at a position spaced from the margin of said zone, causing said substances to undergo diffusion into said zone to react sequentially with said reagent, and subsequently measuring the change in characteristics within said zone caused by the reaction of said indicator substance.

10. The method as claimed in claim 9 in which said indicator substance is radioactively labelled and the characteristic measured is radioactivity, and including the additional step of removing from said zone by diffusion any excess of indicator substance before said radioactivity is measured.

11. The method as claimed in claim 10 in which the test substance is applied to said medium at a position spaced from the margin of said zone and the medium is subjected to electrophoresis to cause said test substance to undergo diffusion into said zone, and an indicator substance in an amount in excess of that capable of reacting with said reagent is applied to said medium at a position spaced from the margin of said zone and caused to undergo diffusion sequentially into said zone by electrophoresis.

* * * * *

UNITED STATES PATENT AND TRADEMARK OFFICE
CERTIFICATE OF CORRECTION

PATENT NO. : 3,966,897
DATED : June 29, 1976
INVENTOR(S) : Donald W. Renn and Calvin A. Saravis It is certified that error appears in the above-identified patent and that said Letters Patent are hereby corrected as shown below:

Under "OTHER PUBLICATIONS", the following references have either been misspelled or dates of publications have been omitted and they should be corrected as follows:

Wide, "Radioimmunoassays Employing Immunosorbents," Acta. Endocrinologica Supplementum, No. 142, 1969, pp. 207-221.

Crowle, "Four Modifications of the Micro Agar Diffusion Precipitin Test," In Journal of Lab. & Clin. Med. vol. 55, No. 4, Apr. 1960, pp. 594-604.

Lehnenger, Albert L., Biochemistry, N.Y., Worth Publishers, Inc., 1970, p. 132.

Column 1, line 13, "Radio-immunoassay" should not be hyphenated; it should read "Radioimmunoassay";

Column 2, line 57, "area" is misspelled;

Column 2, line 66, "greater then" should be "greater than"; same line, after "0.01", insert --micron--;

Column 3, line 21, after "or", insert --by--;

Column 3, line 30, after "present", insert --invention--;

Column 4, line 36, change "the dimension" to --one dimension--;

Column 8, line 54, "hydroxysuccinimide" is misspelled;

Column 9, line 11, "substances" should be --substance--.

Signed and Sealed this

Seventh Day of September 1976

[SEAL]

Attest:

RUTH C. MASON
Attesting Officer

C. MARSHALL DANN
Commissioner of Patents and Trademarks